United States Patent [19]

Young

[11] 4,160,788

[45] Jul. 10, 1979

[54] DISPROPORTIONATION OF TOLUENE

[75] Inventor: Lewis B. Young, Skillman, N.J.

[73] Assignee: Mobil Oil Corporation, New York, N.Y.

[21] Appl. No.: 936,457

[22] Filed: Aug. 24, 1978

[51] Int. Cl.² ............................................. C07C 3/62
[52] U.S. Cl. .................................................... 585/475
[58] Field of Search ..................................... 260/672 T

[56] References Cited

U.S. PATENT DOCUMENTS 3,751,504  8/1973  Keown et al. .................. 260/672 T
4,076,842  2/1978  Plank et al. ......................... 423/329

Primary Examiner—Delbert E. Gantz
Assistant Examiner—C. E. Spresser
Attorney, Agent, or Firm—Charles A. Huggett; Raymond W. Barclay

[57] ABSTRACT

Disproportionation of toluene to produce benzene and xylenes rich in the para isomer is accomplished by subjecting toluene to disproportionation conditions in the presence of a catalyst comprising the crystalline aluminosilicate zeolite ZSM-23.

6 Claims, No Drawings

DISPROPORTIONATION OF TOLUENE

BACKGROUND OF THE INVENTION

1. Field of the Invention

The invention relates to a process for disproportionation of toluene in the presence of specified crystalline aluminosilicate zeolite catalyst to yield benzene and xylenes in which the proportion of para-xylene isomer is substantially in excess of its normal equilibrium concentration.

2. Description of the Prior Art

The disproportionation of aromatic hydrocarbons in the presence of zeolite catalysts has been described by Grandio et al. in the Oil and Gas Journal, Vol. 69, Number 48 (1971).

U.S. Pat. Nos. 3,126,422; 3,413,374; 3,598,878; 3,598,879 and 3,607,961 show vapor-phase disproportionation of toluene over various catalysts.

In these prior art processes, the xylene product produced has the equilibrium composition of approximately 24 percent of para, 54 percent of meta and 22 percent of ortho. Of the xylene isomers, i.e., ortho-, meta- and para-xylene, meta-xylene is the least desired product, with ortho- and para-xylene being the more desired products. Para-xylene is or particular value being useful in the manufacture of terephthalic acid which is an intermediate in the manufacture of synthetic fibers such as "Dacron". Mixtures of xylene isomers either alone or in further admixture with ethylbenzene have previously been separated by expensive superfractionation and multistage refrigeration steps. Such process, as will be realized, has involved high operation costs and has a limited yield.

SUMMARY OF THE INVENTION

In accordance with the present invention, there has been discovered a process for disproportionating toluene to yield benzene and xylenes rich in the para isomer by subjecting toluene to disproportionation conditions in the presence of a catalyst comprising the crystalline aluminosilicate zeolite ZSM-23.

It has been found that such zeolite, particularly in the hydrogen or acid form, has the ability, without further modification, to afford selectively high yields of para-xylene when employed as a catalyst in disproportionation of toluene.

Compared to a conventional thermodynamic equilibrium mixture in which the para:meta:ortho ratio is approximately 1:2:1, the process described herein affords a xylene product in which para-xylene may predominate. The improved yield of para-xylene, generally greater than 50 percent of the total xylene production, compared with approximately 24 percent equilibrium concentration reduces the cost of production and most important the cost of separation of para-xylene from its isomers which is the most expensive step in the current method employed for producing para-xylene.

The present process comprises disproportionation of toluene in the presence of the specified catalyst at a temperature between about 200° C. and about 760° C. at a pressure between atmospheric and about 1000 psig utilizing a feed weight hourly space velocity (WHSV) between about 0.08 and about 20. The latter WHSV is based upon the weight of catalyst composition, i.e., the total weight of active catalyst and binder therefor. The effluent is separated and distilled to remove the desired products of benzene and xylene and unreacted product, i.e., toluene, is recycled for further reaction.

SUMMARY OF SPECIFIC EMBODIMENTS

It is a particular feature of the present invention that a specific crystalline aluminosilicate zeolite, namely ZSM-23, may be effectively employed, without modification, as a catalyst in the disproportionation of toluene to selectively produce para-xylene.

ZSM-23 is described in U.S. Pat. No. 4,076,842 issued Feb. 28, 1978, which descriptive matter is hereby incorporated herein by reference. Particularly ZSM-23 has a composition, expressed in terms of mole ratios of oxides as follows:

(0.5 to 3.0)$R_2O$:(0.08 to 0.4)$M_2O$:$Al_2O_3$:(40 to 250)$SiO_2$ wherein R is a nitrogen-containing cation derived from pyrrolidine and M is an alkali metal cation. It will be noticed that the ratio $R_2O$ to $Al_2O_3$ may exceed unity in this material probably due to the occlusion of excess pyrrolidine species ($R_2O$) within the zeolite pores.

In a preferred synthesized form, the zeolite has a formula, in terms of mole ratios of oxides and in the anhydrous state, as follows:

(0.7 to 2.8)$R_2O$:(0.08 to 0.25)$M_2O$:$Al_2O_3$:(50–220)$SiO_2$ wherein R is a nitrogen-containing cation derived from pyrrolidine, M is an alkali metal, especially sodium.

The original cations of the as-synthesized ZSM-23 can be replaced in accordance with techniques well known in the art, at least in part, by ion exchange with other cations. Preferred replacing cations include metal ions, ammonium ions, hydrogen ions and mixtures thereof. Particularly preferred cations are those which render the zeolite catalytically active. These include hydrogen, rare earth metals, and metals of Groups IIA, IIIB, IVB, VIB, VIII, IB, IIB, IIIA and IVA. In a particularly preferred embodiment, the acid form of ZSM-23 is employed wherein cationic sites are predominately occupied by hydrogen.

The synthetic ZSM-23 zeolite possess a definite distinguishing crystalline structure whose X-ray diffraction pattern shows substantially the significant lines set forth in Table I.

TABLE I

| d(A) | $I/I_o$ |
|---|---|
| 11.2 + 0.23 | Medium |
| 10.1 + 0.20 | Weak |
| 7.78 + 0.15 | Weak |
| 5.59 + 0.10 | Weak |
| 5.44 + 0.10 | Weak |
| 4.90 + 0.10 | Weak |
| 4.53 + 0.10 | Strong |
| 3.90 + 0.08 | Very Strong |
| 3.72 + 0.08 | Very Strong |
| 3.62 + 0.07 | Very Strong |
| 3.54 + 0.07 | Medium |
| 3.44 + 0.07 | Strong |
| 3.36 + 0.07 | Weak |
| 3.16 + 0.07 | Weak |
| 3.05 + 0.06 | Weak |
| 2.99 + 0.06 | Weak |
| 2.85 + 0.06 | Weak |
| 2.54 + 0.05 | Medium |
| 2.47 + 0.05 | Weak |
| 2.40 + 0.05 | Weak |
| 2.34 + 0.05 | Weak |

These values were determined using standard techniques.

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable ions of Groups IB to VIII of the Periodic Table including, by way of example, nickel, zinc, calcium or rare earth metals. Generally, for the purpose of this invention, ZSM-23 will be used in the hydrogen form.

M in the above formula can be one or more of a variety of alkali metal cations, suitably defined as including all alkali metal ions derived from alkali metal oxide or hydroxide as well as alkali metal ions included in alkali metal silicates and aluminates (not including alkali metal salts such as sodium chloride or sodium sulfate which may be derived from neutralization of added inorganic acids such as HCl or $H_2SO_4$ or acid salts such as $Al_2(SO_4)_3$). Non-limiting examples of such suitable alkali metal ions include sodium and potassium.

Zeolite ZSM-23 can be suitably prepared by preparing a solution containing sources of an alkali metal oxide, preferably sodium oxide, pyrrolidine, an oxide of aluminum, an oxide of silicon and water and having a composition, in terms of mole ratios of oxides, falling within the following ranges:

|  | Broad | Preferred |
|---|---|---|
| $R^+/R^+ + M^+$ | 0.77–1.0 | 0.87–0.95 |
| $OH^-/SiO_2$ | 0–0.06 | 0.01–0.055 |
| $H_2O/OH^-$ | 200–1000 | 200–620 |
| $SiO_2/Al_2O_3$ | 50–250 | 50–236 | wherein R is an organic nitrogen-containing cation derived from pyrrolidine and M is an alkali metal ion, and maintaining the mixture until crystals of the zeolite are formed. (The quantity of $OH^-$ is calculated only from the inorganic sources of alkali without any organic base contribution). Thereafter, the crystals are separated from the liquid and recovered. Typical reaction conditions consist of heating the foregoing reaction mixture to a temperature above 280° F. to about 400° F. for a period of time of from about 6 hours to about 14 days. A more preferred temperature range is from about 300° F. to about 375° F. with the amount of time at a temperature in such range being from about 24 hours to about 11 days.

The digestion of the gel particles is carried out until crystals form. The solid product is separated from the reaction medium, as by cooling the whole to room temperature, filtering and water washing.

The crystalline product is dried, e.g., at 230° F., for from about 8 to 24 hours. Of course, milder conditions may be employed if desired, e.g., room temperature under vacuum.

The composition for the synthesis of synthetic ZSM-23 can be prepared utilizing materials which can supply the appropriate oxide. Such compositions include aluminates, alumina, silicates, silica hydrosol, silica gel, silicic acid and hydroxides. It will be understood that each oxide component utilized in the reaction mixture for preparing ZSM-23 can be supplied by one or more essential reactants and they can be mixed together in any order. For example, sodium oxide can be suplied by an aqueous solution of the suitable silicate; the cation derived from pyrrolidine can be either supplied by pyrrolidine or a salt thereof. The reaction mixture can be prepared either batchwise or continuously. Crystal size and crystallization time of the ZSM-23 composition will vary with the nature of the reaction mixture employed.

Synthetic ZSM-23 can have the original cations associated therewith replaced by a wide variety of other cations according to techniques well known in the art. Typical replacing cations include hydrogen, ammonium and metal cations including mixtures thereof.

Typical ion exchange techniques would be to contact the synthetic ZSM-23 zeolite with a salt of the desired replacing cation or cations. Although a wide variety of salts can be employed, particular preference is given to chlorides, nitrates and sulfates.

Representative ion exchange techniques are disclosed in a wide variety of patents including U.S. Pat. Nos. 3,140,249; 3,140,251 and 3,140,253.

Following contact with the salt solution of the desired replacing cation, the zeolite is then preferably washed with water and dried at a temperature ranging from 150° F. to about 600° F. and thereafter is calcined in air or other inert gas at temperatures ranging from about 500° F. to 1500° F. for periods of time ranging from 1 to 48 hours or more to produce a catalytically active thermal decomposition product thereof.

Regardless of the cations replacing the alkali metal in the synthesized form of the ZSM-23, the special arrangement of the aluminum, silicon and oxygen atoms which form the basic crystal lattice of ZSM-23 remains essentially unchanged by the described replacement of alkali metal as determined by taking an X-ray powder diffraction pattern of the ion-exchanged material.

Prior to use, the above-described zeolite catalyst is calcined in an inert atmosphere, e.g., helium or in an oxygen-containing atmosphere, e.g., air. Calcination takes place at a temperature in the approximate range of 500° to 700° C. and preferably between 450° and 550° C.

In practicing the desired disproportionation process it may be desirable to incorporate the zeolite in another material resistant to the temperatures and other conditions employed in the methylation process. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the modified zeolite include those of the montmorillonite and kaoline families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the modified zeolites employed herein may be composited with a porous matrix material, such as silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zirconia. The matrix may be in the form of a cogel. The relative proportions of finely divided zeolite and inorganic oxide gel matrix may vary widely with the zeolite content ranging from between about 1 to about 99 percent by weight and more usually in the range of about 5 to about 80 percent by weight of the composite.

The process of this invention is conducted such that disproportionation of toluene is carried out in the vapor phase by contact in a reaction zone, such as for example, a fixed bed of catalyst, under disproportionation effective conditions, said catalyst preferably being hydrogen exchanged such that a predominate portion of its exchangeable cations are hydrogen ions. In general, it is contemplated that more than 50 percent and preferably more than 75 percent of the cationic sites of the crystalline aluminosilicate zeolite ZSM-23 will be occupied by hydrogen ions. In some instances, it may be desirable to cofeed hydrogen along with toluene to the reaction zone. The presence of hydrogen serves to reduce coke formation and thereby decrease the rate of catalyst aging.

The disproportionation process described herein may be carried out as a batch-type, semi-continuous or continuous operation utilizing a fixed or moving bed catalyst system. A preferred embodiment entails use of a fluidized catalyst zone wherein toluene is passed concurrently or countercurrently through a moving fluidized bed of catalyst. The fluidized catalyst after use is conducted to a regeneration zone wherein coke is burned from the catalyst in an oxygen-containing atmosphere, e.g., air, at an elevated temperature, after which the regenerated catalyst is recycled to the conversion zone for further contact with the toluene feed.

The following examples will serve to illustrate the process of this invention without limiting the same.

EXAMPLE 1

ZSM-23 was prepared by forming a solution of 52.8 grams of sodium aluminate, 10.88 grams of NaOH and 960 grams of water. Then, 582.4 grams of pyrrolidine were added, followed by the addition of 5537.6 grams of collodial silica in 6872 grams of water. The resulting product was mixed until a homogenous gel was formed.

The mixture was stirred at 350° F. for 3 days, during which time crystallization was complete. The product crystals were filtered out of solution and water washed.

X-rays analysis of the crystalline product showed the crystals to have a diffraction pattern corresponding to Table I.

EXAMPLE 2

Toluene was passed over 1.0 gram of the catalyst of Example 1 at a weight hourly space velocity of 5.8 at 560° C. Conversion of toluene was 0.7 weight percent and the concentration of para-xylene in total xylene was 59 percent.

EXAMPLE 3

ZSM-23 was prepared by forming a solution of 13.2 grams of sodium aluminate (43.1% $Al_2O_3$, 33.1% $Na_2O$ and 24.7% $H_2O$), 2.72 grams NaOH (50% solution with water) and 240 grams $H_2O$. Then, 145.6 grams of pyrrolidine were added, followed by the addition of 1318 grams of colloidal silica (30% silica and 70% $H_2O$). The resulting product was mixed until a homogeneous gel was formed. The gel was composed of the following components in mole ratios:

$R^+/R^+ + M^+ = 0.92$ where M is sodium and $R^+$ is the nitrogen-containing cation derived from pyrrolidine $OH^-/SiO_2 = 0.0265$ (not including any contribution of $OH^-$ from pyrrolidine)

$H_2O/OH^- = 371$ (not including any contribution of $OH^-$ from pyrrolidine)

$SiO_2/Al_2O_3 = 118$

The mixture was stirred at 350° F. for 2 days during which time crystallization was complete. The product crystals were filtered out of the solution and water washed continuously for approximately 16 hours and then dried at 230° F.

X-ray analysis of the crystalline product showed the crystals to have a diffraction pattern corresponding to Table I. Additional lines showing the presence of trace amounts of unidentified crystalline material were also observed.

Chemical analysis of the crystalline product led to the following compositional figures:

| Composition | Wt. % | Mole Ratio on $Al_2O_3$ Basis |
|---|---|---|
| C | 4.96 | — |
| N | 1.11 | — |
| Na | 0.27 | — |
| $Al_2O_3$ | 1.65 | 1.0 |
| $SiO_2$ | 96.9 | 101 |
| $N_2O$ | | 2.68 |
| $Na_2O$ | | 0.36 |

Physical analysis of the crystalline product after calcination for 16 hours at 1000° F. showed it to have a surface area of 215 $m^2$/gram and adsorption tests (conducted as described hereinabove) provided the following results:

| Adsorption | Wt. % |
|---|---|
| Cyclohexane | 2.1 |
| n-Hexane | 6.1 |
| Water | 4.6 |

69.7 Grams of ZSM-23 so prepared were heat treated for 3 hours at 1000° F. in nitrogen and then contacted four times at 180°-200° F. with a 10 weight percent solution of $NH_4Cl$, each contact being for a period of 2 hours. The resulting product having a sodium content of 0.03 weight percent was calcined for 10 hours at 1000° F. and thereafter steamed for 20 hours at 1100° F.

EXAMPLE 4

Toluene was passed over 1.6 grams of the catalyst of Example 3 at a weight hourly spaced velocity of 4.7 at 500° C. Conversion of toluene was 3.6 weight percent and the concentration of para-xylene in total xylenes was 41.9 percent.

EXAMPLE 5

Toluene was passed over 1.6 grams of the catalyst of Example 3 at a weight hourly space velocity of 2.4 at 600° C. Conversion of toluene was 10.0 weight percent and the concentration of para-xylene in total xylenes was 36.3 percent.

EXAMPLE 6

The catalyst used in Example 5 was calcined at 600° C. for 1 hour and then toluene was passed thereover under the same conditions used in Example 5. Conversion of toluene was 14.6 weight percent and the concentration of para-xylene in total xylenes was 37.2 percent.

EXAMPLE 7

ZSM-23 in the hydrogen form was prepared by forming a solution of 52.8 grams of sodium aluminate, 10.88 grams of NaOH and 960 grams of water. Then, 582.4 grams of pyrrolidine were added, followed by the addition of 5537.6 grams of colloidal silica in 6872 grams of water. The resulting product was mixed until a homogenous gel was formed.

The mixture was stirred at 350° F. for 3 days, during which time crystallization was complete. The product crystals were filtered out of solution and water washed.

X-ray analysis of the crystalline product showed the crystals to have a diffraction pattern corresponding to Table I.

305 grams of the ZSM-23 so prepared were calcined for 3 hours at 700° F. in nitrogen and then contacted four times at 180°–200° F. with a 10 weight percent solution of $NH_4Cl$ utilizing 10 cc of solution per gram of zeolite, each contact being for a period of 2 hours. The ion exchanged product was then water washed free of chloride, dried at 230° F. and calcined for 10 hours at 1000° F.

EXAMPLE 8

Toluene was passed over 0.3 gram of the catalyst of Example 7 at a weight hourly space velocity of 4.0 at 500° C. Conversion of toluene was 1.6 weight percent and the concentration of para-xylene in total xylenes was 44.0 percent.

EXAMPLE 9

Toluene was passed over 0.3 gram of the catalyst of Example 7 at a weight hourly space velocity of 1.4 at 600° C. Conversion of toluene was 7.5 weight percent and the concentration of para-xylene in total xylenes was 32.6 percent.

EXAMPLES 10–11

Comparative results were obtained for toluene disproportionation at 550° C. and 1 atmosphere toluene employing the catalyst of Example 7 and an HZSM-5 catalyst of similar crystal size.

In conducting these runs, a 250 mg. dried sample of 20/30 mesh catalyst was loaded into a microreactor. The catalyst bed was placed between vycor chips. Toluene was fed with a syringe pump, through a flowmeter and then through a vycor chips-filled preheater. The toluene vapor was vented during flow rate changes and during nitrogen purge of reaction products.

A run consisted of the following steps:
1. Starting at a low WHSV (10).
2. Collecting reaction products at ice bath temperatures for 5–10 minutes.
3. At the end of a run period, directing the toluene vapor to vent. Purging the reaction products to the iced collection vessel with 5cc/min $N_2$.
4. Changing syringe pump setting to increase the WHSV of toluene flow.
5. Discontinuing $N_2$ and beginning toluene flow over catalyst at next WHSV. WHSV generally was varied between 10 and 100. The last run period would be 10 WHSV which would give an idea of activity loss when compared with the first 10 WHSV period.

The results obtained for the ZSM-23 catalyst of Example 7 and an HZSM-5 catalyst of identical 0.02 micron crystal size are shown in the following Table.

TABLE II

| HZSM-23 (Catalyst of Example 7) | | | | | | | | |
|---|---|---|---|---|---|---|---|---|
| WHSV | 2 | 5 | 10 | 20 | 30 | 40 | 50 | 10 |
| Toluene Conv. % | 5.3 | 2.0 | 1.9 | 1.1 | 0.60 | 0.42 | 0.36 | 0.77 |
| p-xylene/total xylenes | 32.9 | 42.8 | 44.0 | 49.6 | 53.4 | 57.8 | 57.1 | 49.6 |
| HZSM-5 | | | | | | | | |
| WHSV | 10 | 20 | 30 | 40 | 50 | 100 | 200 | 10 |
| Toluene Conv. % | 28.3 | 18.1 | 13.0 | 10.0 | 8.2 | 5.1 | 2.6 | 26.8 |
| p-xylene/total xylenes | 23.4 | 24.1 | 24.2 | 24.3 | 24.6 | 25.7 | 27.6 | 23.7 |

It will be seen from the above results that a catalyst of ZSM-23 afforded a substantially higher selective conversion of toluene to para-xylene when compared with a catalyst of ZSM-5, which yielded approximately the normal equilibrium concentration of the para isomer.

It is to be understood that the foregoing description is merely illustrative of preferred embodiments of the invention of which many variations may be made by those skilled in the art within the scope of the following claims without departing from the spirit thereof.

What is claimed is:

1. A process for effecting disproportionation of toluene to produce benzene and xylenes in which the preparation of para-xylene isomer is in excess of its normal equilibrium concentration which comprises contacting toluene under conditions effective for accomplishing said disproportionation in the presence of a catalyst comprising the crystalline aluminosilicate zeolite ZSM-23.

2. The process of claim 1 wherein the disproportionation conditions include a temperature of between about 200° C. and about 760° C., a pressure between atmospheric and 1000 psig and a weight hourly space velocity between about 0.08 and about 20.

3. The process of claim 1 wherein the crystalline aluminosilicate zeolite is combined in an amount between about 1 and about 99 weight percent in a binder therefor.

4. The process of claim 3 wherein said binder is alumina.

5. The process of claim 1 wherein the crystalline aluminosilicate zeolite is predominately in the hydrogen form.

6. The process of claim 5 wherein said crystalline aluminosilicate zeolite is used in combination with a porous matrix.

* * * * *